US012770256B2

(12) United States Patent
Szyc et al.

(10) Patent No.: US 12,770,256 B2
(45) Date of Patent: Oct. 20, 2026

(54) CONTOUR-AWARE PATCH-BASED ANALYSIS OF DERMOSCOPIC IMAGES WITH USER FEATURE SELECTION

(71) Applicant: Magnosco GmbH, Berlin (DE)

(72) Inventors: Lukasz Szyc, Berlin (DE); Eduard Dronnik, Schoenefeld (DE)

(73) Assignee: MAGNOSCO GMBH, Berlin (DE)

( * ) Notice: Subject to any disclaimer, the term of this patent is extended or adjusted under 35 U.S.C. 154(b) by 229 days.

(21) Appl. No.: 18/680,524

(22) Filed: May 31, 2024

(65) Prior Publication Data

US 2024/0404051 A1 Dec. 5, 2024

(30) Foreign Application Priority Data

Jun. 1, 2023 (EP) .................................... 23176655

(51) Int. Cl.

| | |
|---|---|
| ***G06T 7/00*** | (2017.01) |
| ***A61B 5/00*** | (2006.01) |
| ***G06T 7/11*** | (2017.01) |

(52) U.S. Cl.

CPC ............ *G06T 7/0012* (2013.01); *A61B 5/444* (2013.01); *G06T 7/11* (2017.01); *G06T 2207/10056* (2013.01); *G06T 2207/20021* (2013.01); *G06T 2207/20036* (2013.01); *G06T 2207/20092* (2013.01); *G06T 2207/30088* (2013.01); *G06T 2207/30096* (2013.01)

(58) Field of Classification Search

None

See application file for complete search history.

(56) References Cited

U.S. PATENT DOCUMENTS

| | | | | |
|---|---|---|---|---|
| 10,085,643 | B2 * | 10/2018 | Bandic | A61B 5/4875 |
| 11,636,288 | B2 * | 4/2023 | Faust | G06V 10/25 382/128 |
| 2009/0327890 | A1 | 12/2009 | Mertz et al. | |
| 2011/0301441 | A1 * | 12/2011 | Bandic | A61B 5/4875 600/306 |
| 2016/0275681 | A1 | 9/2016 | D'Alessandro | |
| 2018/0218496 | A1 * | 8/2018 | Sinai | G06T 7/0012 |
| 2020/0272864 | A1 * | 8/2020 | Faust | G06N 3/08 |
| 2024/0404051 | A1 * | 12/2024 | Szync | A61B 5/748 |
| 2025/0185915 | A1 * | 6/2025 | Fett | A61B 5/443 |

OTHER PUBLICATIONS

Gokrale M et al: "A visualization oriented data mining tool for biomedical images", Information Reuse and Integration, 2003. IRI 2003. IEEE International Conference on Oct. 27-29, 2003, Piscataway, NJ, USA, IEEE, Oct. 27, 2003 (Oct. 27, 2003), pp. 219-226.

European Search Report mailed Oct. 10, 2023 in EP 23176655.1.

* cited by examiner

*Primary Examiner* — Tahmina N Ansari

(74) *Attorney, Agent, or Firm* — Fox Rothschild LLP

(57) ABSTRACT

The present disclosure provides systems, devices, and methods for adjusting an analysis of a dermoscopic image of a skin lesion, including obtaining the dermoscopic image, detecting morphological features of the skin lesion within the dermoscopic image, displaying the detected features to a user, obtaining from the user information indicative of a selection of one or more of the detected features, and analyzing the dermoscopic image based on the information indicative of a selection of one or more of the detected features and/or based on the selected one or more detected features and presenting an outcome of the analysis to the user.

14 Claims, 10 Drawing Sheets

CONTOUR-AWARE PATCH-BASED ANALYSIS OF DERMOSCOPIC IMAGES WITH USER FEATURE SELECTION

FIELD OF THE INVENTION

The present invention pertains to the field of analyzing dermoscopic images.

TECHNOLOGICAL BACKGROUND

The field of dermatology has seen significant advancement in recent years with the introduction of dermoscopy, a diagnostic tool that allows for a magnified view of the skin's surface and sub-surface structures.

The technique, also known as dermoscopy or epiluminescence microscopy, typically involves the use of a handheld device with a polarized light source that illuminates the skin, allowing for a more detailed examination of skin lesions. Dermoscopy has been proven to be an effective tool for the early detection of various skin conditions, including melanoma, the deadliest form of skin cancer.

The integration of digital imaging technology into dermoscopy has led to the development of computer-aided diagnosis (CAD) algorithms for the analysis of dermoscopic images. These algorithms have the potential to provide a more objective and accurate analysis of skin lesions than traditional visual inspection methods. Furthermore, the use of CAD algorithms can also increase the efficiency of the diagnostic process by reducing the time required for image analysis and allowing for the storage and retrieval of images for future reference.

Despite the growing interest in the use of CAD for dermoscopic image analysis, the development of effective algorithms and methods remains a challenging task. This is due to the complexity and variability of skin lesions, as well as the variability in dermoscopic imaging techniques, the wide range of skin types and conditions, and the limited amount of annotated data available for training algorithms.

There is hence a need for more reliable techniques for the analysis of dermoscopic images in order to improve the accuracy of skin lesion diagnosis, improve the trust of professionals in the analysis methods, and further train the methods to become more accurate.

DESCRIPTION OF INVENTION

The problems of the prior art are overcome or at least reduced by aspects of the present disclosure as given in the appended claims, the following description and preferred embodiments.

According to an aspect of the present disclosure, there is provided a method for adjusting an analysis of a dermoscopic image of a skin lesion. The method includes obtaining a dermoscopic image of a skin lesion, detecting morphological features of the skin lesion within the dermoscopic image, displaying the detected features to a user, obtaining from the user information indicative of a selection of one or more of the detected features, and analyzing the dermoscopic image based on the information indicative of a selection of one or more of the detected features and presenting an outcome of the analysis to the user.

According to some embodiments, the analysis outcome includes a likelihood indicator for the type of lesion in the dermoscopic image.

According to some embodiments, the detected features include dermoscopic features, attributes of dermoscopic features, and/or clusters of dermoscopic features.

A dermoscopic feature includes, for example, a dot, clod, pseudopod, structureless, circle, or blood vessel.

An attribute of a dermoscopic feature includes one or more attributes related to a dermoscopic feature, such as a symmetry, color, thickness, and/or or location. According to some embodiments, certain attributes are more clinically relevant, and thus have higher importance, in relation to some dermoscopic features than other dermoscopic features. For example, a color feature attribute is highly relevant to a clod dermoscopic feature, a thickness feature attribute is highly relevant to a line dermoscopic feature, and a location feature attribute is highly relevant to a structureless dermoscopic feature.

A cluster of dermoscopic features refers to properties of a plurality of dermoscopic features, for example, a pattern formed by a plurality of dermoscopic features.

According to some embodiments, feature selection refers to a selection of a feature category, wherein a feature category selection indicates that the entire feature category is to be included or excluded. For example, a user feature selection could refer to the user indicating that the category of a shapes, colors, size, or patterns is to be excluded from the analysis.

According to some embodiments, feature selection refers to a selection within a feature category, wherein a selection within a feature category indicates that the one or more instances of a feature within a feature category is to be included or excluded. For example, a user feature selection could refer to the user indicating that within the category of colors, a specific color is to be excluded from the analysis.

According to some embodiments, feature selection refers to a selection of an instantiation of a feature within the image, such that, if multiple instances of a particular feature are detected, a user can select one or more of the instances to be included or excluded from the analysis. For example, if multiple instances of a pattern are detected in a lesion, the user may select one or more instances of the specific patterns to be included in the analysis, while selecting one or more of the other instances to be excluded from the analysis.

Advantageously, providing the user with the detected morphological features indicates the internal state of a device or a computer implementing the method or performing operations corresponding to the method by specifying to the user which features are successfully detected and which features are involved in the analysis.

Advantageously, separating the computational load into two stages reduces computation cost compared to utilizing a large unstaged model. Particularly, a first stage relates to of the detecting of morphological features, then, a second stage of performing an analysis based on the morphological features selected by the user within the detected morphological features. As used herein, a selection of features by a user can refer to an editing of feature selection, for example, feature selection by a user can include unselecting features that were preselected or selecting features that were not preselected. Furthermore, by preferably only analyzing the specific morphological features selected by the user, rather than processing the entire image, the computation is further optimized.

Advantageously, the user feature selection process increases the interpretability of the analysis results, making it easier for users to understand and interpret the generated analysis outcome.

Furthermore, the obtained user selection of features facilitates training the method to provide more relevant feature selection in further uses thereof.

As used herein, the term "dermoscopic image" refers to an image of the skin, commonly a high-resolution, magnified image of the skin, obtained using a device called a dermoscope. The term "dermoscopic image" refers to a type of close-up, detailed image that provides a clearer and more comprehensive view of the skin and its features, including skin lesions. Dermoscopic images are commonly used in dermatology to help diagnose and evaluate skin conditions, as they provide a more detailed and accurate representation of the skin compared to traditional images. Commonly, dermoscopic images are obtained by placing a small, handheld device called a dermoscope directly on the skin and observing the skin through a magnifying lens. Dermoscopes typically include one or more illumination sources, such as light-emitting diodes, to provide the homogeneous intense illumination required to obtain a high-quality image of a region of interest. There are two main modes of contact dermoscopy: Polarised dermoscopy (PD) and non-polarised dermoscopy (NPD).

The main difference between non-polarized dermoscopy (NPD) and polarized dermoscopy (PD) is the depth of visualized structures. While NPD is better for inspecting structures in the superficial skin layers (e.g., superficial epidermis down to the dermo-epidermal junction [DEJ]), PD is better for evaluating the deeper skin layers (e.g., DEJ and superficial dermis).

Polarised and nonpolarised dermoscopy are to some extent complementary and the combination of both methods increases diagnostic accuracy and clinician confidence.

As used herein, the term "morphological features" refers to distinct physical attributes or characteristics of a skin lesion that can be observed in a dermoscopic image. These features include, but are not limited to:

- Shape: The overall shape of the lesion, such as circular, irregular, or polygonal.
- Size: The dimensions of the lesion, including width, length, and depth.
- Texture: The surface characteristics of the lesion, such as smooth, rough, or bumpy.
- Color: The hue, saturation, and brightness of the lesion, including the presence of any discoloration or pigmentation.
- Arrangement: The arrangement of structures or patterns within the lesion, such as dots, streaks, or lines.
- Border: The outline or contour of the lesion, including features such as jagged edges, irregular margins, or clear borders.

Those morphological features in general can be categorized into dermoscopic features, dermoscopic feature attributes, and attributes of clusters of dermoscopic features.

Dermoscopic features refer to the structures observed in a skin lesion. Examples of dermoscopic features include the presence and structure of pigmentation, the presence of vascular structures, and the like. Dermoscopic feature attributes refer to the specific characteristics of each dermoscopic feature. Attributes of clusters of dermoscopic features refer to the spatial relationships between multiple dermoscopic features within a lesion.

As used herein, the expression "type of the lesion" refers to the clinical classification or categorization of a skin lesion based on its specific characteristics defined or characterized by morphological features. The term "type of the lesion" can refer to a range of skin conditions, including but not limited to:

- Benign (non-cancerous) lesions: Examples include warts such as seborrheic keratosis, freckles such as solar lentigo, and the vast majority of various kind of melanocytic nevi (moles), including the most common type known as Clark nevus
- Malignant (cancerous) lesions: Examples include basal cell carcinoma, squamous cell carcinoma, and melanoma.
- Inflammatory lesions: Examples include dermatitis, psoriasis, and rosacea.
- Infectious lesions: Examples include cold sores, impetigo, and warts caused by human papillomavirus (HPV).

Some of the skin lesions such as actinic keratoses may be considered as precancerous (pre-malignant). Precancerous conditions of the skin is a condition, tumor or lesion involving abnormal cells (e.g. keratinocytes) which are associated with an increased likelihood of developing into cancer.

According to some embodiments, the analysis comprising generating an indicator, or an indicator with a respective likelihood, of a lesion type in the dermoscopic image can be achieved by analyzing one or more morphological features such as color, shape, structure, and pattern associated with specific characteristics of the lesion type.

According to some embodiments, a feature related to colors is included in the analysis for generating an indicator of a lesion type or a likelihood thereof in the dermoscopic image.

According to some embodiments, a feature related to shapes is included in the analysis for generating an indicator of a lesion type in the dermoscopic image. For example, a round or oval shape is often seen in benign lesions, while irregular shapes are commonly associated with malignant lesions. The shape is particularly relevant in relation to a thickness of a line or a shape of a clod.

According to some embodiments, a feature related to structures is included in the analysis for generating an indicator of a lesion type in the dermoscopic image. For example, the presence of parallel lines, dots, and globules can indicate a specific type of lesion, while the absence of these structures can suggest a different type.

According to some embodiments, a feature related to patterns is included in the analysis for generating an indicator of a lesion type in the dermoscopic image, forming a dermoscopic pattern analysis which can be utilized for differential diagnostics. For example, a pattern symmetry or color symmetry are analyzed for providing indication of a lesion type.

According to some embodiments, after detecting morphological features of the skin lesion within the dermoscopic image, the detected features are presented/displayed to a user, preferably together with the image, preferably in an overlay manner, to facilitate feature selection by the user.

Advantageously, the user can select, based on the image and their assessment thereof, whether certain morphological features need to be excluded or weighted down in the analysis. Thereby increasing the accuracy of the analysis by incorporating information obtained based on the knowledge and experience of the user.

According to some embodiments, analyzing the dermoscopic images involves the use of machine learning. Different types of machine learning models can be used, for example, in some embodiments, a supervised machine learning model is utilized, which is trained using labeled input and output data sets. These data sets may include dermoscopic images with associated features and an indicator for the type of lesion in the image. Alternatively, an unsupervised machine learning model may be used, which is trained using raw or unlabeled data. In this case, the machine learning algorithm automatically classifies the dermoscopic images based on patterns and structures within the data.

According to some embodiments, analyzing dermoscopic images is performed through the use of decision trees. This involves generating a tree-like model that maps features of the image to a decision regarding the type of lesion present. Decision trees can be constructed through a variety of methods, including through the use of supervised machine learning techniques such as classification and regression trees (CART), or through unsupervised methods such as clustering. Once constructed, the decision tree can be applied to new dermoscopic images.

According to some embodiments, an analysis involving one or more features includes a combination of one, two, three, four, five, or more features.

According to some embodiments, the analysis is performed using a predetermined number of features. According to some embodiments, different importance values are assigned to different morphological features, and the analysis of the dermoscopic image is based on selecting a predetermined number of features with the highest importance values among the selected features.

According to some embodiments, the predetermined number of features for analysis is in the range of 2 to 5. According to some embodiments, the predetermined maximum number of features (patterns) for analysis is 3.

According to some embodiments, an analysis of both the color and pattern of a lesion is performed to determine the type of the lesion.

According to some embodiments, detecting morphological features of the skin lesion within the dermoscopic image involves extracting certain features from the dermoscopy images that can be used to distinguish between lesions.

According to some embodiments, one or more of the following techniques is used for detecting/extracting morphological features:

- Edge detection—Edge detection algorithms such as Canny, Sobel, and Roberts can be used to identify boundaries between different regions in the image. These boundaries can provide information about the shape and texture of lesions.
- Texture analysis—Texture analysis techniques such as Gabor filters, Laws masks, and Local Binary Patterns (LBP) can be used to capture the texture of lesions. These techniques are useful for identifying patterns in the image that are not easily noticeable to the human eye.
- Color analysis—Color analysis is used to detect differences in color and intensity between different regions in the image. This information can be used to identify different types of lesions.
- Shape analysis—Shape analysis techniques such as contour detection, Fourier descriptors, and Hu Moments are used to quantify the shape of lesions. These techniques provide information about the size, orientation, and symmetry of lesions.
- Scale-invariant feature transform (SIFT)—SIFT is a feature detection algorithm that is invariant to changes in scale, orientation, and illumination. This makes it useful for identifying distinctive features in images that can be used to differentiate between different types of lesions.
- Speeded-up robust features (SURF)—SURF is a feature detection algorithm similar to SIFT that is faster and more robust. It is used for detecting distinctive features in images and is especially useful for detecting lesions in images with complex backgrounds.

According to some embodiments, the information indicative of a selection of one or more of the detected features includes a checklist, item selection, drag-and-drop selection, removal of non-selected features, or the like. For example, the features could be presented to the user in multiple layers/hierarchies, wherein, in the highest hierarchy, different dermoscopic features categories are presented, then specific features attributes related to the dermoscopic features are presented. According to some embodiments, a feature selection of the user refers to a selection or deselection of one or more of a dermoscopic feature and/or a feature attribute.

According to some embodiments, the method further comprises analyzing the dermoscopic image based on the detected features to generate a preliminary analysis outcome, before obtaining from the user information indicative of a selection of one or more of the detected features, wherein displaying the detected features to a user comprises further displaying the outcome of the preliminary analysis to the user.

According to some embodiments, the preliminary analysis outcome is a preliminary indicator for the type or class of lesion in the dermoscopic image or a likelihood thereof, wherein the preliminary indicator includes, for example, a class clue, clues for a particular class, a feature or a particular features that are associated with or indicative of a particular class.

Advantageously, the preliminary analysis in addition to the detected features based on which the preliminary analysis is performed provides the user with an outcome of the method prior to the intervention of the user while indicating to the user the features based on which the analysis was performed, thereby still providing the user with the internal state of a device performing the method or performing computations or operations corresponding to the method.

According to some embodiments, visual cues are provided to the user indicating how different feature selections would affect the outcome of the analysis.

According to some embodiments, the method includes the step of performing preprocessing on the dermoscopic image.

According to some embodiments, the preprocessing includes image normalization, involving converting the image to a standard format to ensure that it can be processed by the computer and analyzed accurately. This includes converting the image to a standard size and converting the color space to a format that is more suitable for analysis, such as grayscale or RGB.

According to some embodiments, the preprocessing includes image enhancement, involving improving the visibility of the features of the lesion in the image. This can be achieved using techniques such as contrast enhancement, smoothing, and edge detection to make the features of the lesion more distinguishable.

According to some embodiments, the preprocessing includes image segmentation, involving separating the lesion from the background in the image. This can be achieved using techniques such as thresholding, clustering, and morphological operations to identify the lesion and eliminate the background.

According to some embodiments, the method further comprises, before detecting features of the dermoscopic image, segmenting the obtained image to segments of interest, displaying the result of the segmentation to the user, and obtaining from the user a confirmation of the segmentation or correction information for the segmentation, wherein analyzing the dermoscopic image is further based on the segmentation.

Advantageously, the preprocessing, particularly the segmentation, defines an area within the entire image for feature extraction, thereby improving the accuracy and reducing the computational workload of the method.

According to some embodiments, the method is further configured to obtain segmentation information from the user, for example, by obtaining a contour/line drawn or adjusted by the user.

According to some embodiments, the image, or parts thereof, such as a segment or parts of a segment, are divided into a plurality of patches, wherein each patch or at least one or some of the patches are analyzed individually for extracting morphological information therefrom.

According to some embodiments, the analysis of one or more patches is modified based on an analysis of adjacent or neighboring patches or based on information related to a segment or lesion to which the patch belongs.

According to some embodiments, the analysis of one or more patches is modified based on the location of at least one patch in relation to the lesion or parts thereof. Particularly, according to some embodiments, the location of at least one patch in relation to the lesion or parts thereof includes the distance of the patch from a detected edge of the lesion.

For example, a feature detected in a patch, for example, a pattern, gradient, shape, or color, in an initial analysis, could be altered in the modified analysis based on the location of the patch in relation to the contour/boundaries of the lesion, such that, one or more features could be provided more weight/importance based on the patch being in close proximity to the contour or the lesion while being provided less weight/importance based on the patch being located near the center of the lesion. According to some embodiments, one or more features could be provided more weight/importance based on the patch being located near the center of the lesion while being provided less weight/importance based on the patch being in close proximity to the contour or the lesion.

According to some embodiments, analyzing the dermoscopic image is further based on the analysis and/or the modified analysis of at least one patch.

According to some embodiments, at least some adjacent patches are overlapped. According to some embodiments, at least some adjacent patches do not overlap.

According to some embodiments, detecting features of the dermoscopic image comprises inputting the image to an AI feature detection model.

According to some embodiments, detecting features of the dermoscopic image comprises utilizing Convolutional Neural Networks (CNNs), specifically designed to analyze image data. The CNNs can be used to detect various morphological features in the dermoscopic image, such as color, texture, and pattern. For example, a CNN can be trained on a large dataset of dermoscopic images to identify specific patterns in the image that are indicative of different types of lesions. Alternatively, visual transformer-based architectures are used for feature detection.

According to some embodiments, detecting features of the dermoscopic image comprises utilizing Transfer Learning, where a pre-trained AI model is used as a starting point for further training on a new dataset. For example, a pre-trained CNN that has been trained on a large dataset of natural images can be used as a starting point for further training on a smaller dataset of dermoscopic images for feature detection.

According to some embodiments, analyzing the dermoscopic image involves the utilization of a plurality of computational modules, wherein one or more of the computational modules is/are associated with one or more morphological features.

According to some embodiments, analyzing the dermoscopic image based on the information indicative of a selection of one or more of the detected features and/or based on the detected features includes activating computational modules corresponding to the detected features and deactivating computational modules corresponding to non-selected features, and generating the likelihood indicator for the type of the lesion in the dermoscopic image based on outcomes of the activated computational modules, preferably, wherein a computational module is a branch in a decision tree.

According to some embodiments, feature selection refers to a selection of a feature category, wherein a feature selection indicates that the entire feature is to be included or excluded.

According to some embodiments, feature selection refers to a selection of an instantiation of a feature within the image, such that, if multiple instances of a particular feature are detected, a user can select one or more of the instances to be included or excluded from the analysis. For example, if multiple instances of a pattern are detected in a lesion, the user may select one or more instances of the specific patterns to be included in the analysis, while selecting one or more of the other instances to be excluded from the analysis.

According to some embodiments, the deactivation of a computational module refers to assigning a low weight, a weight below a certain threshold, or a zero weight to the deactivated computational module. According to some embodiments, a computational module is a branch in a decision tree model.

According to some embodiments, activation of a computational module refers to assigning a high weight or a weight above a certain threshold to the activated computational module.

According to some embodiments, analyzing the dermoscopic image comprises utilizing a computational architecture in which multiple modules are operated and combined to form a single result, which is the likelihood indicator for a type of lesion in the dermoscopic image.

For example, one model might be trained to predict the likelihood of a lesion being melanoma based on the color and texture of the lesion, while another model might be trained to predict the likelihood based on the shape and size of the lesion. The final prediction could be made by taking a weighted average of the predictions from all the models, with more weight given to the models that perform better on a validation set. According to some embodiments, the model is configured to perform an analysis based on the selection of one feature, such as a selection of one of a color, shape, texture, or size.

Advantageously, the use of models in this way can provide a more accurate prediction of the type of lesion than it would be possible with a single model. This is because the models can capture different aspects of the morphological features that are relevant to the classification of the lesion, and the combination of their predictions can reduce the effects of overfitting and improve the overall accuracy of the prediction.

Additionally, such an architecture is advantageous for facilitating an altered analysis of the image based on the feature selection.

According to some embodiments analyzing the dermoscopic image comprises providing the detected and/or selected features to a decision-tree model. Correspondingly, a likelihood indicator for a type of lesion in a dermoscopic image can be generated by providing selected morphological features to a decision-tree model. When provided with a set of morphological features, such as shape, color, size, and texture, the model is able to accurately classify the type of lesion present in the image. Advantageously, decision trees can be visualized, thereby providing valuable information to the user on the state of the computer performing the analysis, particularly by presenting the factors and underlying reasoning behind a model's predictions.

According to some embodiments, in the analysis of dermoscopic images, weighted clues can be utilized to improve the accuracy of the analysis. Weighted clues refer to assigning different weights or importance to different features or segments of the image based on their relevance to the outcome. For example, certain morphological features may be more indicative of a particular type of lesion than others, and therefore, given a higher weight in the analysis. Similarly, different segments of the image may have varying degrees of relevance to the diagnosis, such as the center of the lesion versus the surrounding tissue. By incorporating weighted clues into the analysis, the machine method can more effectively identify patterns and structures within the image that are indicative of specific types of lesions.

According to some embodiments, the decision-tree model is built by splitting the feature set into distinct branches. Each branch includes a set of conditions that must be met in order to classify the lesion. For example, a decision-tree model may split the feature set based on the presence or absence of certain colors, shapes, or textures. If a certain set of morphological features is present, the model will classify the lesion as belonging to a particular type or provide a likelihood indicator for the type of lesion.

When generating a likelihood indicator for a type of lesion, the decision-tree model is used to evaluate the detected and/or selected morphological features of the lesion and determine the probability that it belongs to a particular type.

According to some embodiments, the dermoscopic image is a polarized dermoscopy, PD, image. Advantageously, polarized dermoscopy is used to enhance the contrast of dermoscopic images and to improve the visualization of skin structures. This technique involves the use of polarized light, which is commonly generated by a special filter that is placed in front of the dermoscope.

As used herein, The term "Polarized Light Dermoscopy" (PD) refers to a method that uses a polarized light source and detector. This method typically involves using one or more illumination sources, like light-emitting diodes, to provide even and bright lighting for high-quality PD images of a specific area. In PD, the light that reflects back from the skin surface to the detector must pass through a polarizer that blocks photons of the original light source's polarization (known as cross-polarization), which reduces unwanted surface glare. If the originally polarized light scatters enough in the skin, it can create "polarization randomization," which allows back-reflected "deep penetrating light" to pass through the cross-polarizing filter and enter the eye or detector. This enables the visualization of dermoscopic structures from the stratum granulosum of the epidermis through the dermal-epidermal junction to the superficial dermis.

According to some embodiments, displaying the detected features includes overlaying the detected features on the dermoscopic image, preferably wherein one or more of the features is highlighted, colored in, outlined, cut out, and/or marked with a symbol.

According to some embodiments, there is provided a device for indicating a likelihood of a skin condition in an image, including a display, a user input mechanism, and a processor configured to perform operations corresponding to any of the preceding methods.

According to some embodiments, the device further includes a communication unit configured to obtain the dermoscopic image from an external device.

According to some embodiments, there is provided system comprising the device as described above and the external device as described above.

According to some embodiments, there is provided a computer program comprising instructions which, when executed by a computer, cause the computer to carry operations corresponding to any of the preceding methods.

Certain embodiments of the present disclosure may include some, all, or none of the above advantages. One or more technical advantages may be readily apparent to those skilled in the art from the figures, descriptions, and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by the study of the following detailed descriptions.

BRIEF DESCRIPTION OF THE DRAWINGS

Examples illustrative of embodiments are described below with reference to the figures attached hereto. In the figures, identical structures, elements, or parts that appear in more than one figure are generally labeled with the same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE DRAWINGS

In the following description, various aspects of the disclosure will be described. For the purpose of explanation, specific configurations, and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Figure 1:
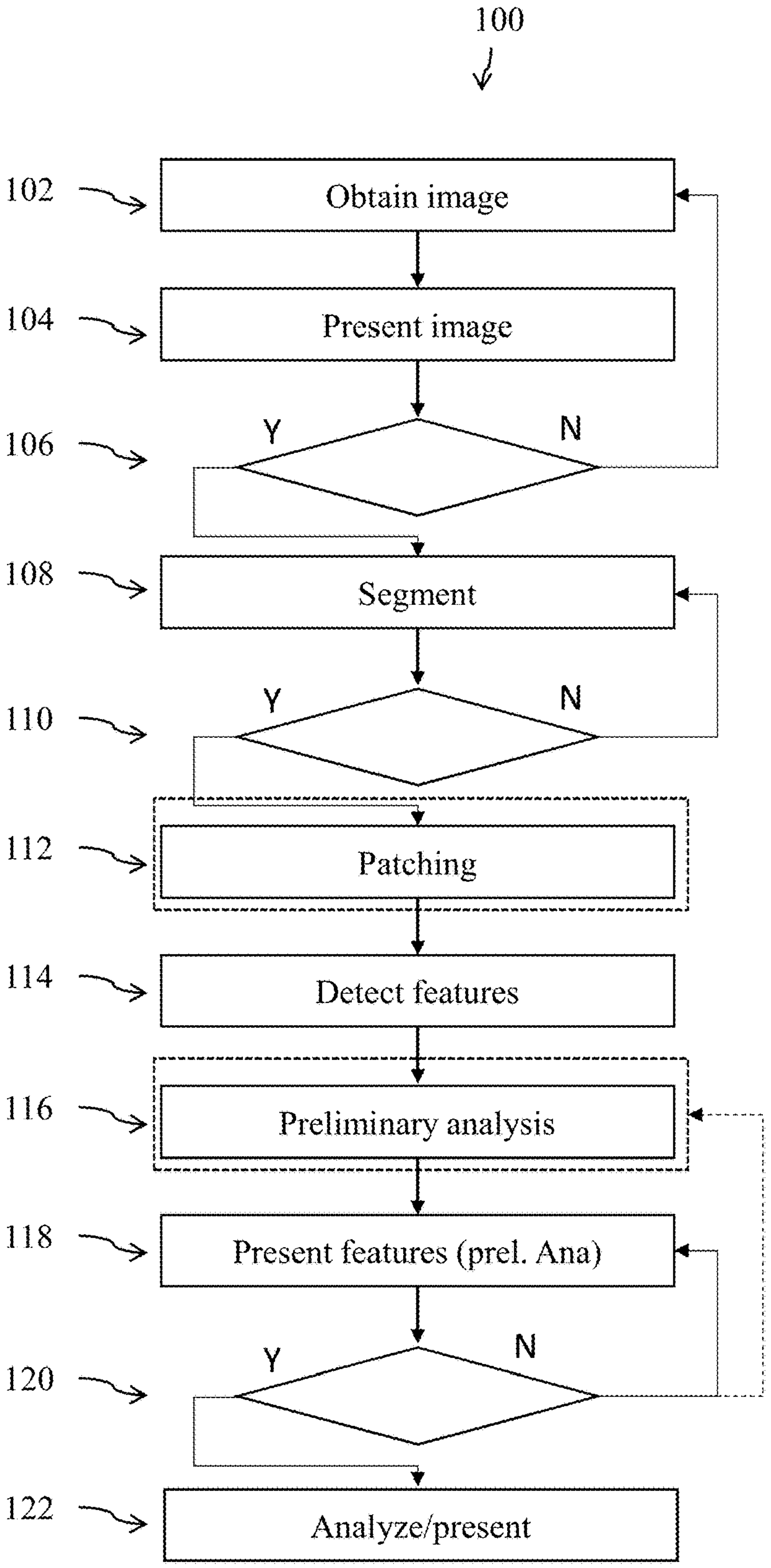
FIG. 1 schematically illustrates a method for analyzing a dermoscopic image, according to some embodiments.

Reference is now made to FIG. 1, which schematically illustrates a method 100 for analyzing a dermoscopic image, according to some embodiments. Initially, the dermoscopic image is obtained 102, for example, by directly capturing the dermoscopic image or by receiving the dermoscopic image from an external device such as a server or from a cloud database, then, the image is presented to the user 104 via a display/monitor, and the input of the user is received as to whether the image is confirmed or declined 106.

The user may determine to decline the image if the quality of the image is insufficient. If the user decides to decline the image, a new image is obtained 102 by retrieving a different image, or, alternatively, by performing preprocessing on the image, such as noise reduction or sharpening, and reintroducing the preprocessed image to the user 104.

If the user determines that the image is confirmed, the method proceeds to segmenting the image 108 into one or more segments, wherein each segment includes a potential lesion. Then, the user assesses the segmentation 110 and provides feedback as to whether the segmentation is confirmed or declined.

If the user declines the segmentation, the user can manually select segments, for example by drawing outlines of segments, selecting specific segments from the suggested segments, and/or adjusting segment outlines for one or more of the provided segments.

Once the segmentation is confirmed, the method 100 optionally proceeds with dividing the one or more segments into patches 112, which are analyzed for detecting morphological features 114 and presenting the detected morphological features to the user 118. Optionally, the method further includes performing a preliminary analysis 116 based on the detected features and presenting the results of the predetermined analysis to the user together with the detected features based on which the preliminary analysis is performed 118.

The user selects one or more of the detected features 120 and decides whether to perform another preliminary analysis 116 or to perform a complete analysis 122 of the image based on the selected features.

According to some embodiments, in the case of only the pseudopods pattern being present in the image, the selection of location attribute from circumferential to segmental changes the analysis outcome from Reed nevus to Melanoma.

According to some embodiments, the method includes training one or more machine learning modules based on the input of the user at specific input stages. According to some embodiments, the method includes training an image quality assessment module based on the decisions of the user of confirming or declining images. According to some embodiments, the method includes training a segmentation module based on the feedback provided by the user on the segmentation of one or more images. According to some embodiments, the method includes training a feature detection/extraction module based on the feedback provided by the user on the presented features.

Figure 2:
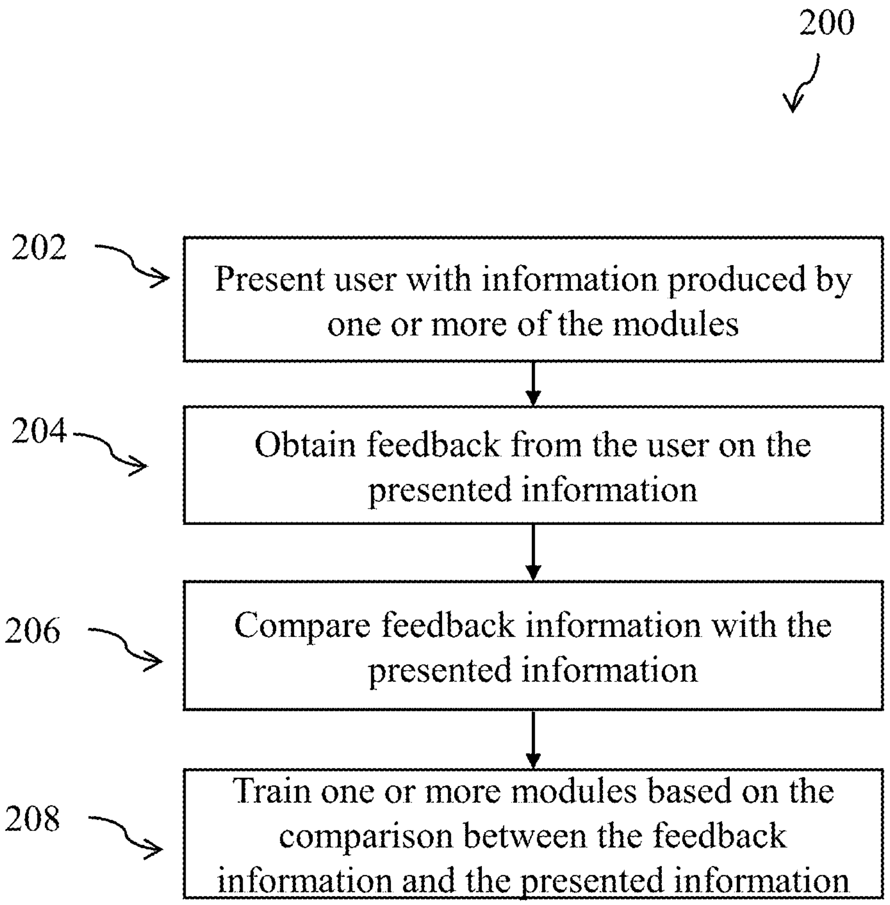
FIG. 2 schematically illustrates a method for training computational modules for analyzing a dermoscopic image, according to some embodiments.
Figure 3A:
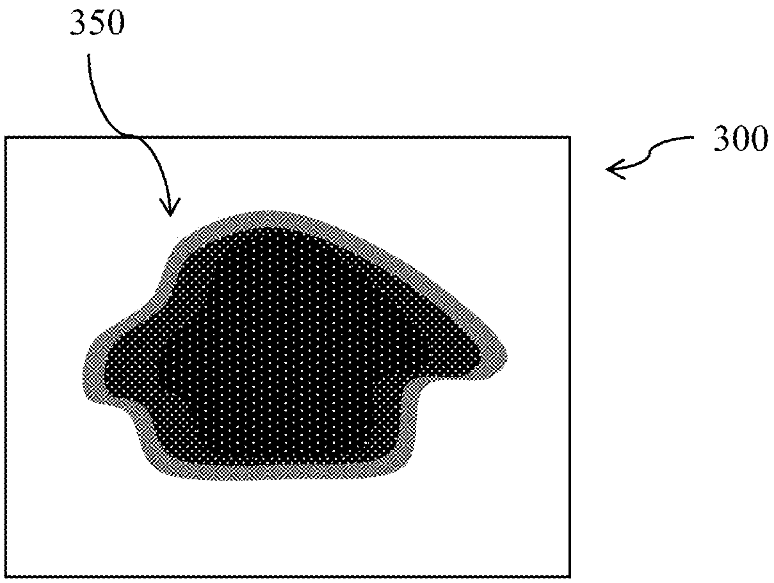
FIGS. 3*a*, 3*b*, 3*c*, and 3*d* illustrate different stages in a method of analyzing a dermoscopic image, according to some embodiments.
Figure 3B:
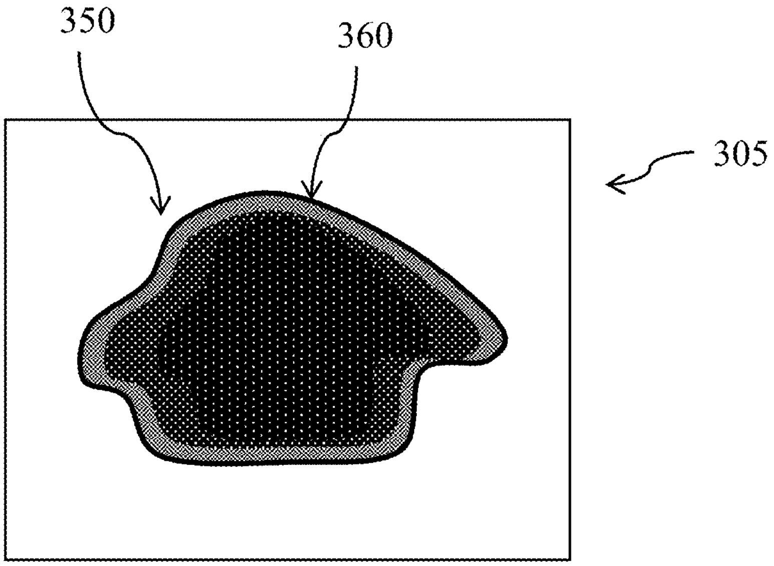
Figure 3C:
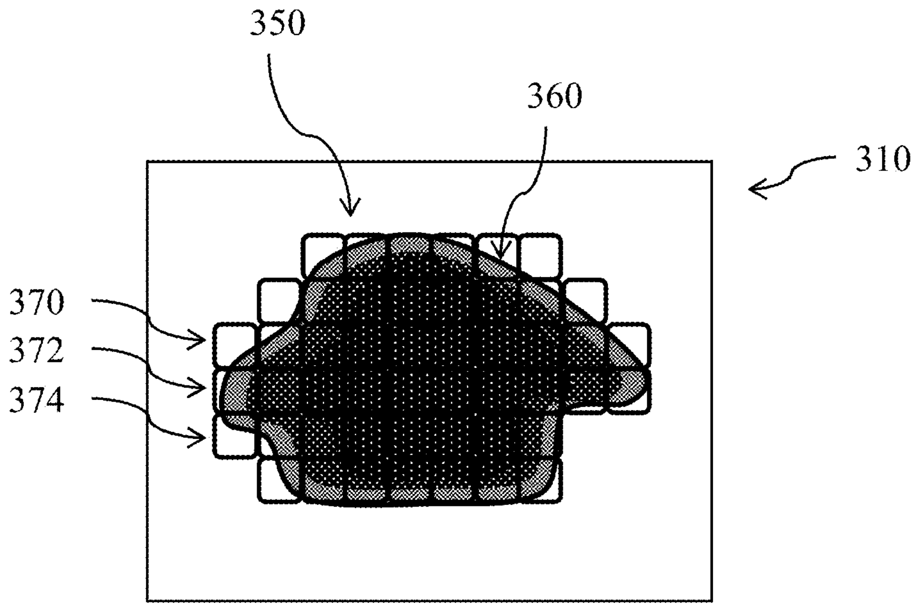
Figure 3D:
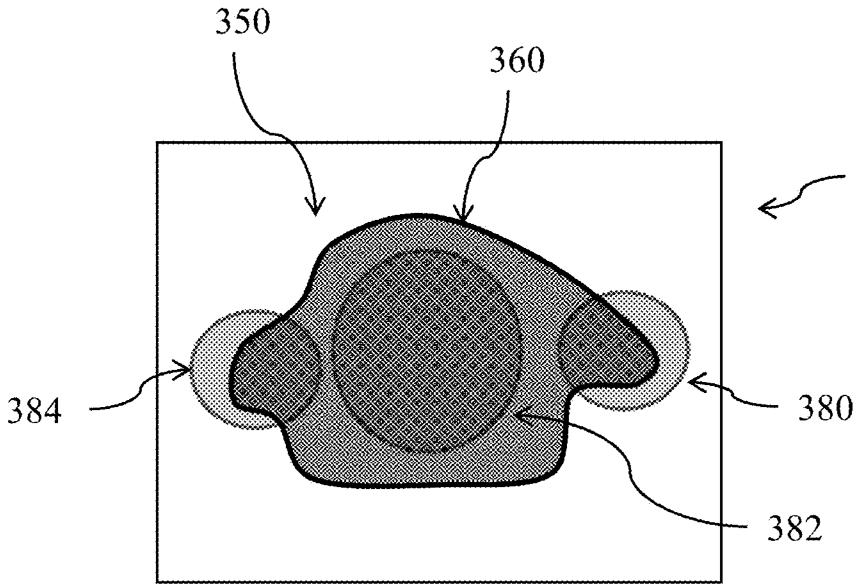

Reference is now made to FIG. 2, which schematically illustrates a method 200 for training computational modules for analyzing a dermoscopic image, according to some embodiments. Initially, the user is presented with information produced by one or more modules 202, for example, segmentation information from a segmentation module and/or detected features from a feature detection module. Then, feedback from the user is obtained based on the presented information 204. The feedback is then compared with the presented information 206 for training one or more modules based on the comparison between the feedback information and the presented information 208.

Reference is now made to FIGS. 3*a*, 3*b*, 3*c*, and 3*d*, which illustrate different stages 300, 305, 310, and 315, in a method of analyzing a dermoscopic image, according to some embodiments.

In the initial stage 300, a dermoscopic image including a lesion 350 is presented to the user for an overall assessment of the image. The user may determine that the quality of the image is insufficient, for example, because the lighting conditions are not proper, the lesion is not completely presented in the image, or the image is too blurry. A rejected image may be disposed of, and a new image is presented to the user. Alternatively, the image undergoes image enhancement preprocessing, for example, based on the feedback provided by the user.

If the user confirms the presented image, the segmentation stage 305 takes place, in which the contour 360 or contours of one or more lesions is detected and presented to the user. Advantageously, the contour 360 is presented to the user together with the lesion 350. Conveniently, the contour 360 is overlayed on the lesion 350.

The user, presented with the segmented image, provides feedback related to the segmentation. Particularly, the user can approve of the provided segmentation, adjust the segmentation by selecting specific segments, adjust the segmentation by altering/editing the contours of one or more segments, and/or drawing a contour of a segment not provided in the initial segmentation.

Then, the segmented image undergoes a patching process in a patching stage 310, wherein the one or more of the segments 360 corresponding to a lesion 350 are divided into a plurality of patches, such as patches 370, 372, and 374, which are analyzed for detecting morphological features in the lesion. Advantageously, performing morphological feature detection on patches simplifies the feature detection/extraction process and enables parallelizing the process for enhanced efficiency. These advantages apply also for the training phase.

According to some embodiments, the patches are collected from the image on a regular grid with constant step size. At each step, a patch of predefined window-size is extracted. According to some embodiments, many patches are merged to a batch of a predefined size before being analysed by an artificial neural network for feature detection. For each patch a feature-wise outcome is calculated, while batching provides a method for parallelizing the patch analysis.

According to some embodiments, the patches are analyzed in an initial analysis individually, then, the patches are re-analyzed based on the analysis of adjacent/neighboring patches and/or based on the location of each of the patches in relation to the lesion, for example, based on the distance of each of the patches from the contour of the lesion.

Then, based on the analysis of the patches, one or more morphological features are detected/extracted from the image and presented to the user in a feature selection stage 315, in which the user selects one or more features such as features 380, 382, and/or 384, based on which the analysis of the image is performed for generating a likelihood indicator for a type of the lesion in the dermoscopic image.

According to some embodiments, the patched image is provided to the user for patch selection. According to some embodiments, a patch selection is provided by selecting or not selecting one or more patches. According to some embodiments, a patch selection is provided in a rule-based manner, for example, patches conforming with a specific rule, such as distance from the contour, are selected, while other patches are not selected.

According to some embodiments, the user provides feature selection indication for specific patches, such as particular selected patches or patches meeting certain criteria.

For example, one or more of the features 380, 382, and/or 384 is a feature related to symmetry, patterns, and or color. For example, features 380, 382, and/or 384 refer to specific features from different categories, such as pattern, gradient, shape, or color. In another example, features 380, 382, and/or 384 refer to different instances of a specific feature, for example, a specific pattern detected in multiple instances.

Figure 4:
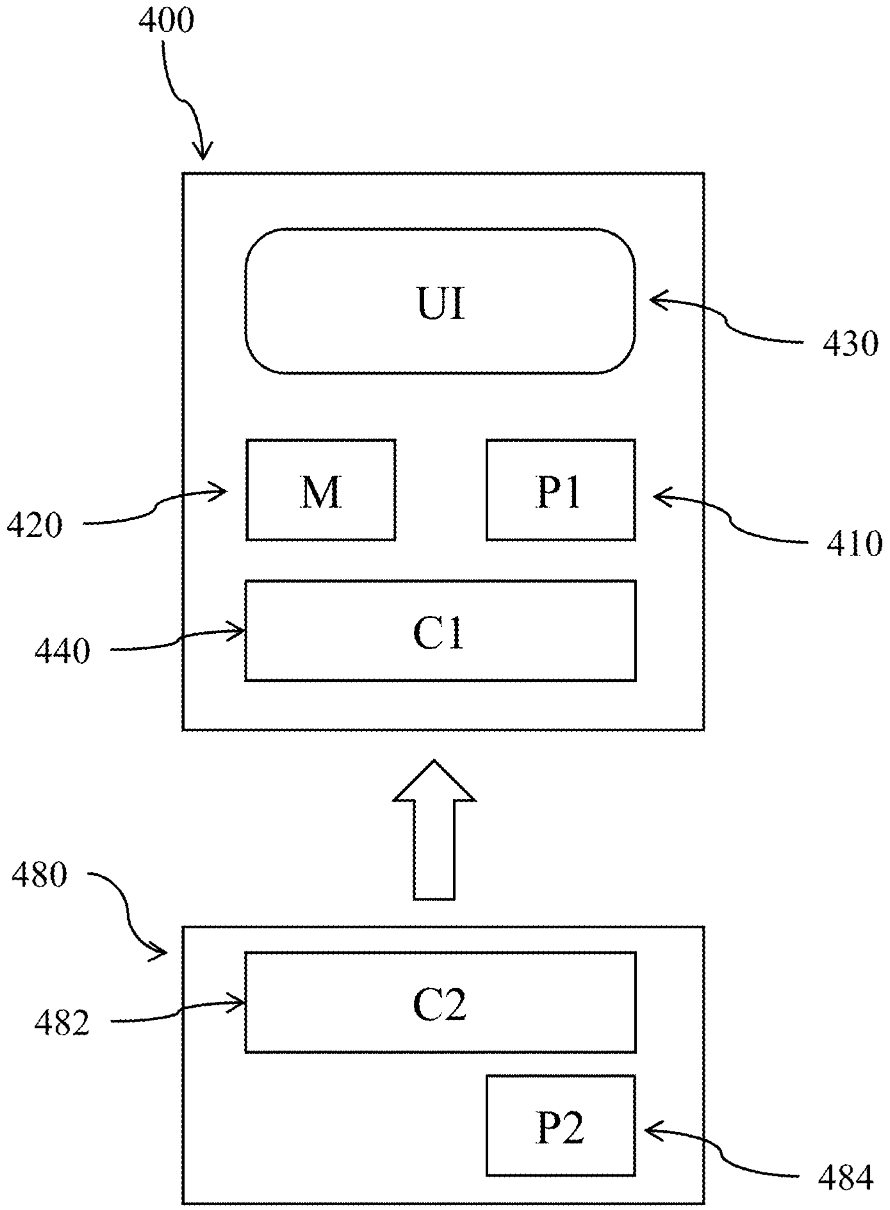
FIG. 4 schematically illustrates a device for analyzing a dermoscopic image, according to some embodiments.

Reference is now made to FIG. 4, which schematically illustrates a system comprising a device 400 for analyzing a dermoscopic image, according to some embodiments. The device includes a processor 410 configured to perform operations corresponding to the methods brought herein, and memory 420 configured to store instructions operable by the processor 410 and at least one dermoscopic image to be analyzed. The device further includes a user interface module 430 configured to display information to the user and obtain inputs from the user, such as the selection of segments, selection of features, and the like.

While the user interface module 430 is depicted as one module, it represents any number of components adapted to present information to the user and receives information from the user, such as a display, a speaker, light indicators, a microphone, a touch-screen, one or more buttons, a control column, or the like.

According to some embodiments, the device 400 further includes a communication module 440, configured to communicate with an external device 480 via an external communication module 482 in the external device 480 for receiving information, such as configuration information and/or data such as a dermoscopic image or update the information to one or more computational modules in the device.

According to some embodiments, the method, or at least parts thereof, is performed using multiple computational modules, wherein at least some of the computational modules are specialized to perform an analysis based on a specific morphological feature.

According to some embodiments, the morphological feature selection affects the activation or deactivation of the corresponding computational modules.

Figure 5A:
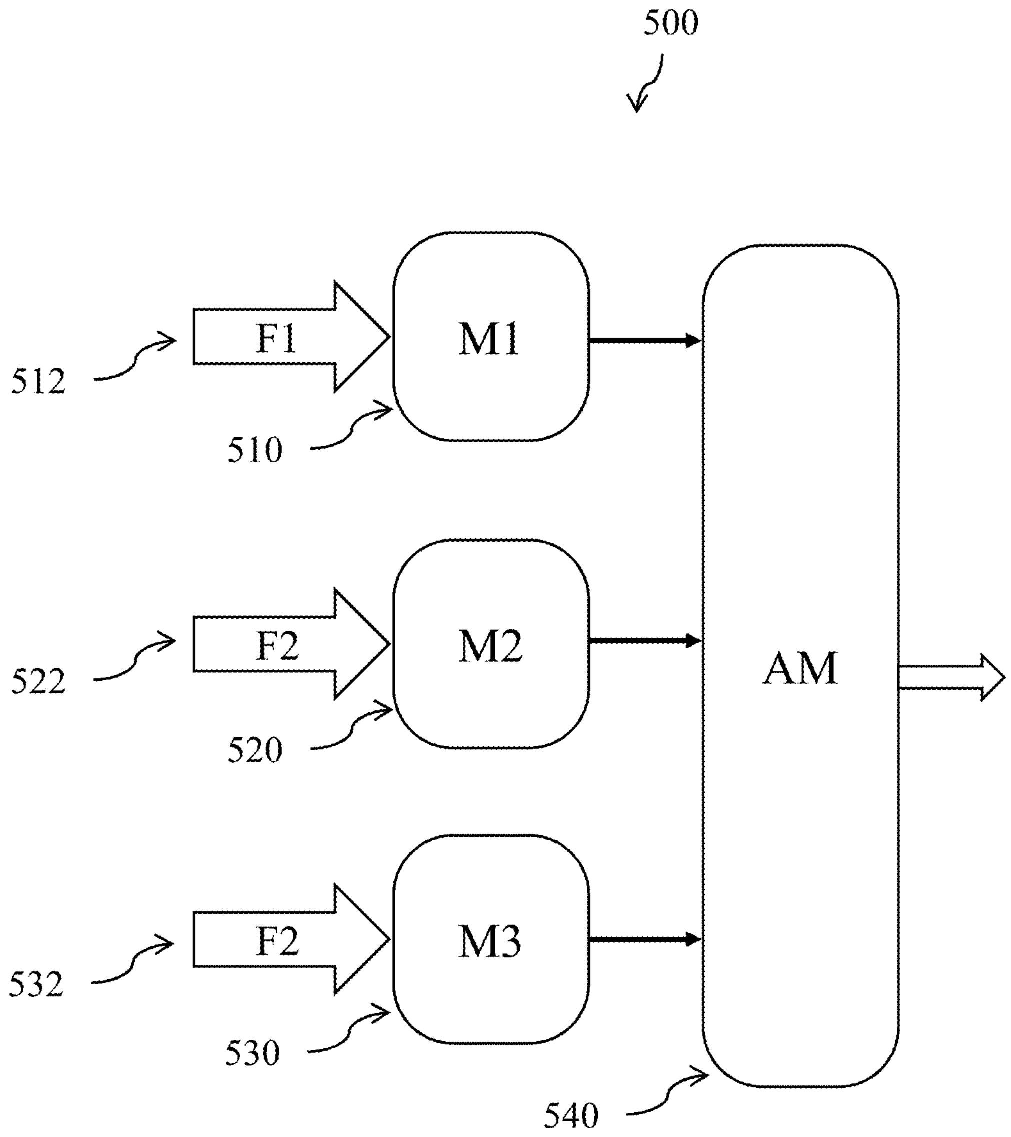
FIGS. 5*a* and 5*b* schematically illustrate a parallel computational architecture for analyzing a dermoscopic image, according to some embodiments.
Figure 5B:
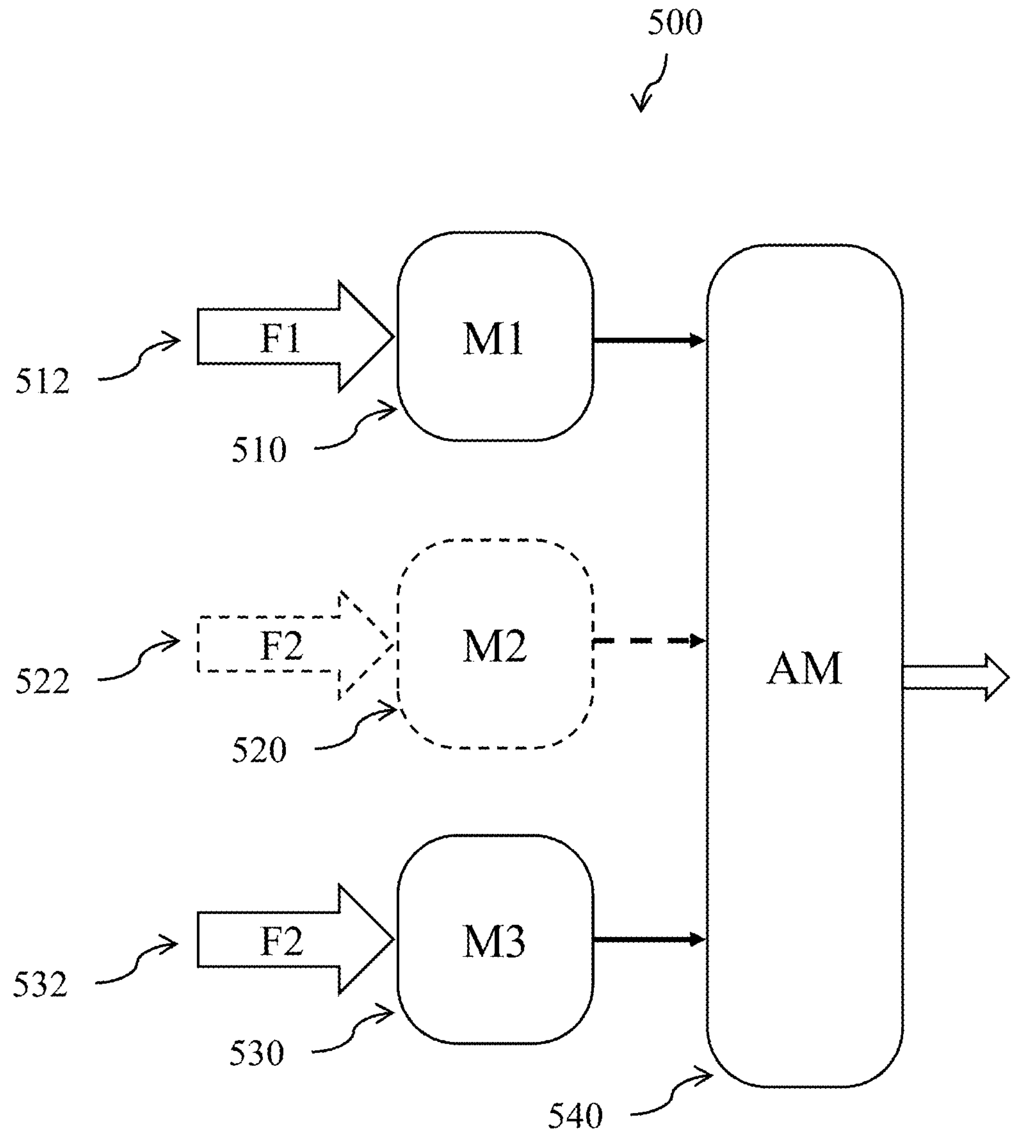

Reference is now made to FIGS. 5*a* and 5*b*, which schematically illustrate a parallel computational architecture 500, such as a decision tree structure, for analyzing a dermoscopic image, according to some embodiments. The architecture 500 includes multiple computational modules, for example, a first specialized module 510, a second specialized module 520, and a third specialized module 530, wherein each of the specialized modules is specifically trained and/or configured to perform analysis operations based on a corresponding morphological feature. The specialized modules can be, for example, different branches in a decision tree model.

The first specialized module 510 receives a first data 512 as an input, the second specialized module 520 receives a second data 522 as an input, and the third specialized module 530 receives a third data 532 as an input.

The first data 512, second data 522, and third data 532 can be the same data, for example, the dermoscopic image. Alternatively, the first data 512, second data 522, and third data 532 are different from one another and are tailored for the respective specialized module. The tailoring to the respective specialized module can be achieved by providing an image with a specific resolution, spectrum, filter, preprocessing, or the like.

The outputs of the first specialized module 510, second specialized module 520, and third specialized module 530 are provided to an aggregation computational module 540, configured to generate a likelihood indicator for a type of lesion in the dermoscopic image based on the received outputs.

Exemplary, the first specialized module 510 is specialized to analyze color features of the image or a patch in the image and to classify the color to one of pale pink, pink, red, purple, yellow, brown, black, blue, or white.

Exemplary, the second specialized module 520 is specialized to analyze shape features of the image or a patch in the image and to classify shapes as discoid, oval, annular, arcuate, or targetoid.

Exemplary, the third specialized module 530 is specialized to analyze arrangements of lesions in the image or a patch in the image and to classify distributions, such as grouped lesions, discrete/isolated lesions, linear/streak lesions, dermatomal lesions, serpiginous lesions, reticular lesions, symmetrical lesions, or photo-distributed lesions.

In FIG. 5*a*, all of the first specialized module 510, second specialized module 520, and third specialized module 530 are activated and are involved in the analysis process.

In contrast, FIG. 5*b* depicts a situation in which the first specialized module 510 is activated, the second specialized module 520 is deactivated, and the third specialized module 530 is activated, for example, as a result of feature selection performed by the user. In such a case, predominantly the features associated with the activated specialized modules affect the outcome of the analysis.

Figure 6A:
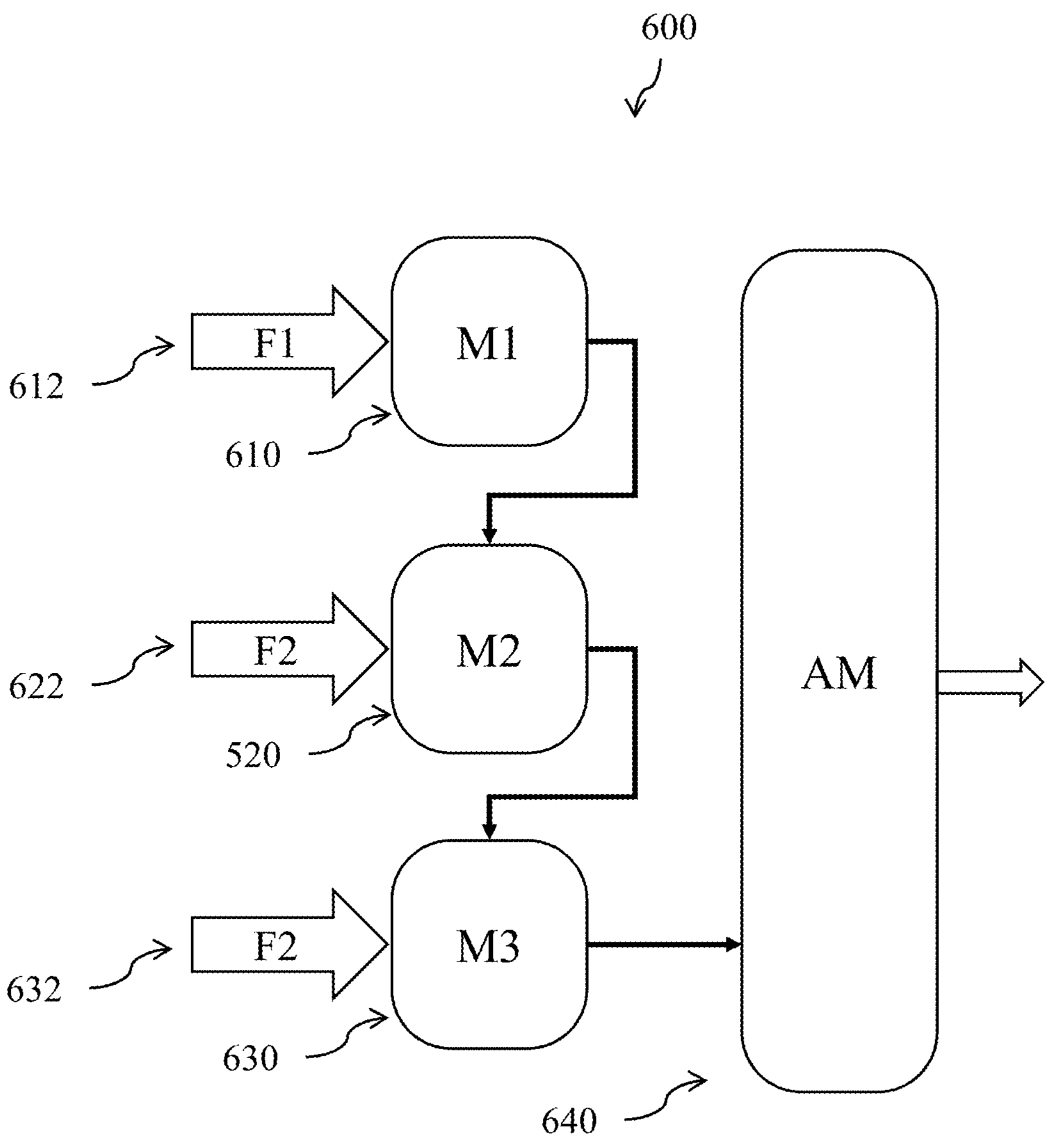
FIGS. 6*a* and 6*b* schematically illustrate a serial computational architecture for analyzing a dermoscopic image, according to some embodiments; and, FIG. 7 schematically illustrates a hybrid parallel and serial computational architecture for analyzing a dermoscopic image, according to some embodiments.
Figure 6B:
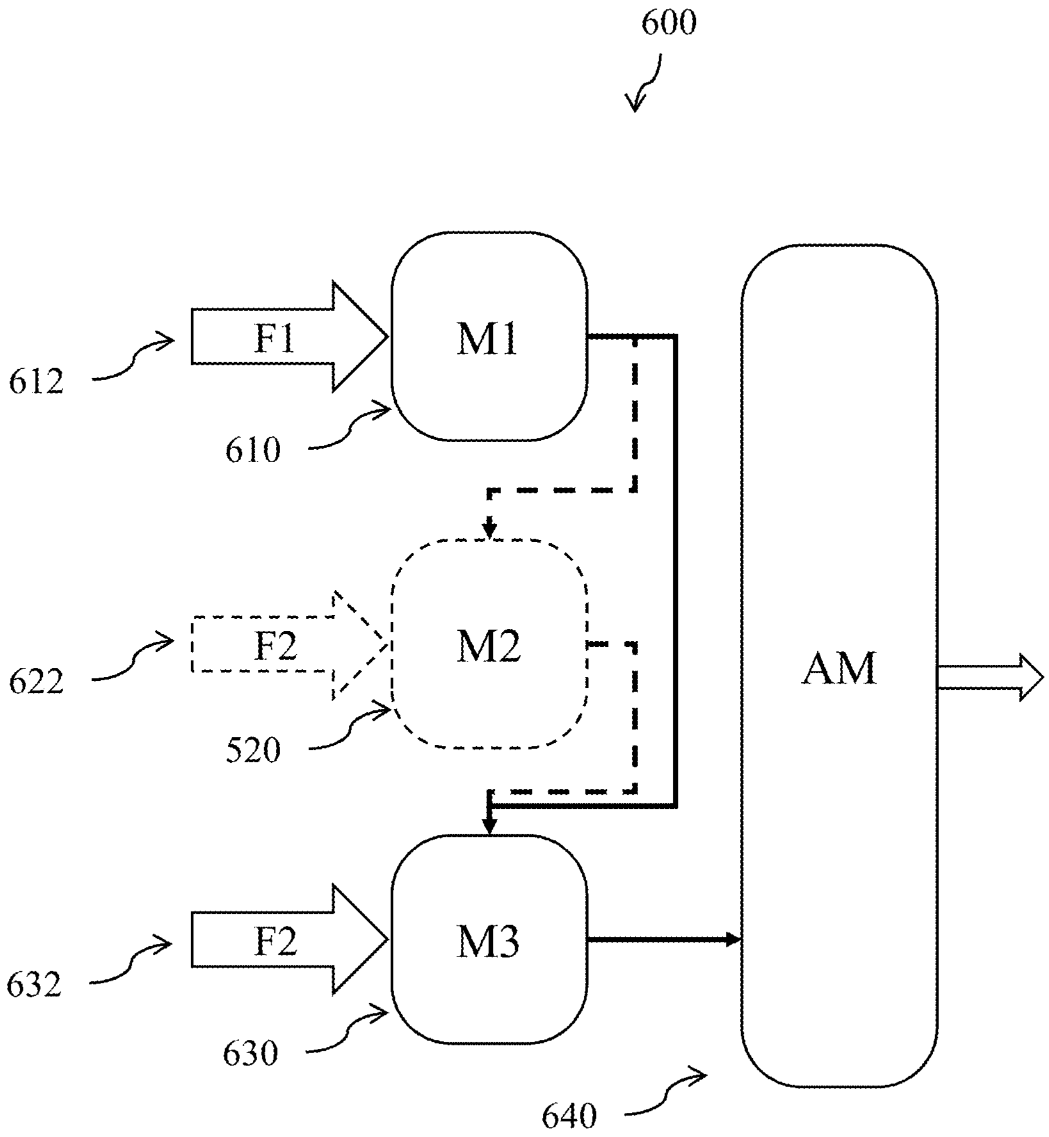

Reference is now made to FIGS. 6*a* and 6*b*, which schematically illustrate a serial computational architecture 600 for analyzing a dermoscopic image, according to some embodiments. The architecture 600 includes multiple computational modules, for example, a first specialized module 610, a second specialized module 620, and a third specialized module 630, wherein each of the specialized modules is specifically trained and/or configured to perform analysis operations based on a corresponding morphological feature.

The first specialized module 610 receives a first data 612 as an input, the second specialized module 620 receives a second data 622 as an input in addition to an output of the first specialized module 610, and the third specialized module 630 receives a third data 632 as an input in addition to the output of the second specialized module 620.

The first data 612, second data 622, and third data 632 can be the same data, for example, the dermoscopic image. Alternatively, the first data 612, second data 622, and third data 632 are different from one another and are tailored for the respective specialized module. The tailoring to the respective specialized module can be achieved by providing an image with a specific resolution, spectrum, filter, pre-processing, or the like.

The output of the third specialized module 630 is provided to an aggregation computational module 640, configured to generate a likelihood indicator for a type of lesion in the dermoscopic image based on the received output. According to some embodiments, the aggregation computational module 640 and one or more of the specialized modules, for example, the third specialized module 630, form one module, The first specialized module 610, second specialized module 620, and third specialized module 630 can be configured corresponding to the first specialized module 510, second specialized module 520, and third specialized module 530 as brought in FIGS. 5*a* and 5*b*, particularly with regards to the specialization thereof.

In FIG. 6*a*, all of the first specialized module 610, second specialized module 620, and third specialized module 630 are activated and are involved in the analysis process.

In contrast, FIG. 6*b* depicts a situation in which the first specialized module 610 is activated, the second specialized module 620 is deactivated, and the third specialized module 630 is activated, for example, as a result of feature selection performed by the user. In such a case, predominantly the features associated with the activated specialized modules affect the outcome of the analysis.

According to some embodiments, hybrid architectures are implemented for performing the analysis based on the feature selection.

Figure 7:
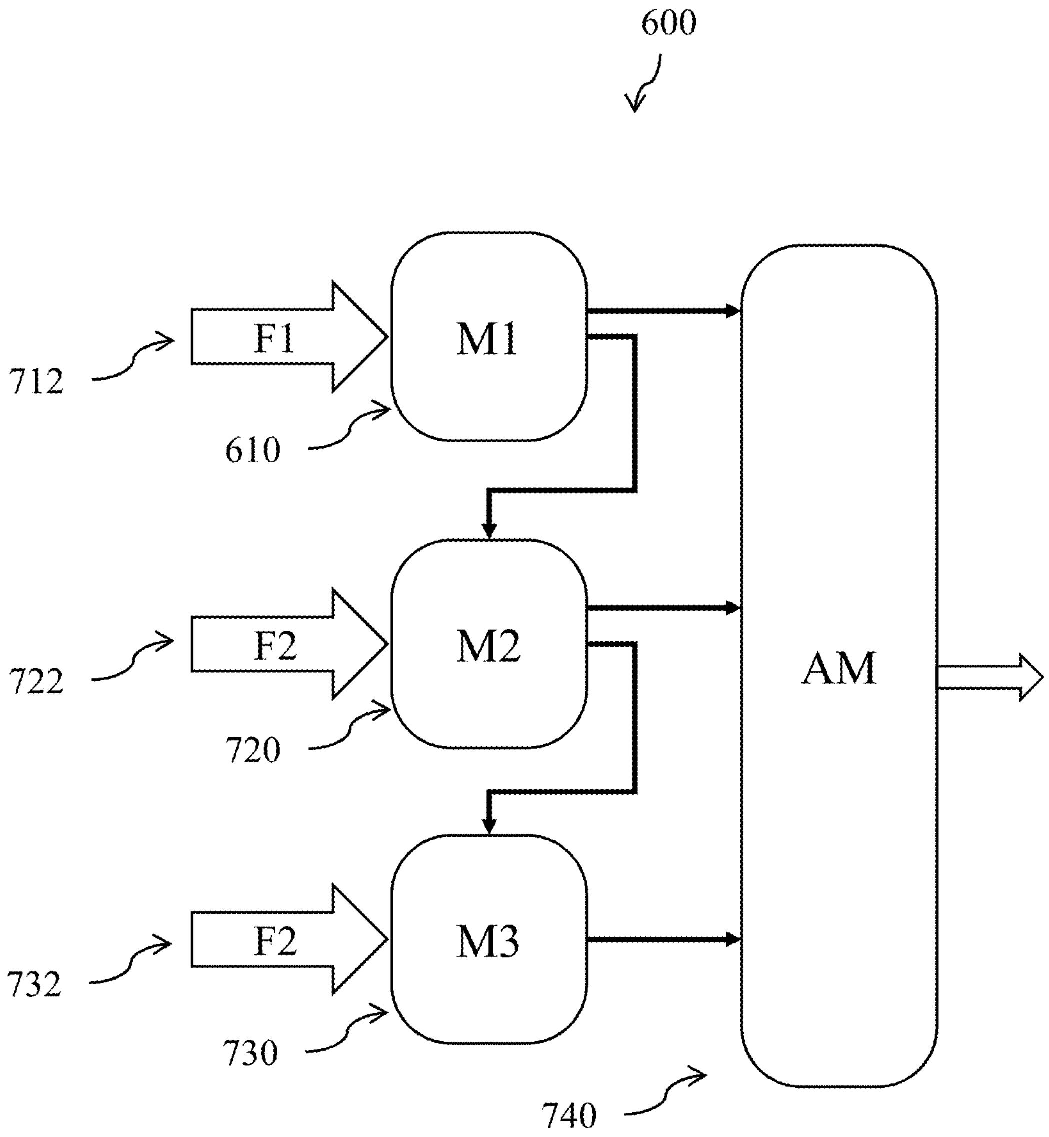

Reference is now made to FIG. 7, which schematically illustrates a hybrid parallel and serial computational architecture 700 for analyzing a dermoscopic image, according to some embodiments. The architecture 700 includes multiple computational modules, for example, a first specialized module 710, a second specialized module 720, and a third specialized module 730, wherein each of the specialized modules is specifically trained and/or configured to perform analysis operations based on a corresponding morphological feature.

The first specialized module 710 receives a first data 712 as an input, the second specialized module 720 receives a second data 722 as an input in addition to an output of the first specialized module 710, and the third specialized module 730 receives a third data 732 as an input in addition to the output of the second specialized module 720.

The first data 712, second data 722, and third data 732 can be the same data, for example, the dermoscopic image. Alternatively, the first data 712, second data 722, and third data 732 are different from one another and are tailored for the respective specialized module. The tailoring to the respective specialized module can be achieved by providing an image with a specific resolution, spectrum, filter, pre-processing, or the like.

The outputs of the first specialized module 710, second specialized module 720, and third specialized module 730 are provided to an aggregation computational module 740, configured to generate a likelihood indicator for a type of lesion in the dermoscopic image based on the received outputs.

The first specialized module 710, second specialized module 720, and third specialized module 730 can be configured corresponding to the first specialized module 510, second specialized module 520, and third specialized module 530 as brought in FIGS. 5*a* and 5*b*, particularly with regards to the specialization thereof.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. In addition, the term "plurality" may be used throughout the specification to describe two or more components, devices, elements, parameters, and the like.

Embodiments of the present disclosure may include apparatuses for performing the operations herein. This apparatus may be specially constructed for the desired purposes, or it may comprise a general-purpose computer selectively activated or reconfigured by a computer program stored in the computer. Such a computer program may be stored in a computer-readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read-only memories (EEPROMs), magnetic or optical cards, or any other type of media suitable for storing electronic instructions, and capable of being coupled to a computer system.

The disclosure may be described in the general context of computer-executable instructions, such as program modules, being executed by a computer. Generally, program modules include routines, programs, objects, components, data structures, and so forth, which perform particular tasks or implement particular abstract data types. The disclosure may also be practiced in distributed computing environments where tasks are performed by remote processing devices that are linked through a communications network. In a distributed computing environment, program modules may be located in both local and remote computer storage media including memory storage devices.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions, and sub-combinations thereof. It is therefore intended that the following appended claims and claims hereafter introduced be interpreted to include all such modifications, additions, and sub-combinations as are within their scope.

REFERENCE SIGNS

100, 200 method
102, 104, 106, 108, 110, 112, 114, 116, 118, 120, 122, 202, 204, 206, 208 method steps
300, 305, 310, 315 stage

350 lesion
360 segmentation
370, 372, 374 patch
380, 382, 384 feature
400 device
410 processor
420 memory
430 user interface
440 communication module
480 external device
482 communication module
484 processor
500, 600, 700 computational architecture
510, 520, 530, 610, 620, 630, 710, 720, 730 specialized module
512, 522, 532, 612, 622, 632, 712, 722, 732 data
540, 640, 740 aggregation module

The invention claimed is:

1. A method for adjusting an analysis of a dermoscopic image of a skin lesion, comprising:
obtaining the dermoscopic image,
detecting morphological features of the skin lesion within the dermoscopic image,
displaying the detected features to a user,
obtaining from the user information indicative of a selection of one or more of the detected features, and
analyzing the dermoscopic image based on the information indicative of a selection of one or more of the detected features and/or based on the selected one or more detected features and presenting an outcome of the analysis to the user,
wherein analyzing the dermoscopic image comprises:
dividing the dermoscopic image to a plurality of patches,
analyzing at least one of the patches individually, and
modifying the analysis of the at least one patch based on the location of the at least one patch in relation to a contour of the lesion.

2. The method of claim 1, further comprising:
analyzing the dermoscopic image based on the detected features to generate a preliminary analysis outcome, before obtaining from the user information indicative of a selection of one or more of the detected features,
wherein displaying the detected features to a user comprises further displaying the preliminary analysis outcome to the user.

3. The method of claim 1, further comprising:
assigning different importance values to the morphological features,
wherein analyzing the dermoscopic image is based on selecting a predetermined number of features with the highest importance values among the selected features.

4. The method of claim 1, further comprising, before detecting features of the dermoscopic image:
segmenting the obtained image to segments of interest,
displaying the result of the segmentation to the user, and
obtaining from the user a confirmation of the segmentation or correction information for the segmentation,
wherein analyzing the dermoscopic image is further based on the segmentation.

5. The method of claim 1, wherein at least two of the plurality of patches partially overlap.

6. The method of claim 1, wherein detecting features of the dermoscopic image comprises inputting the image to an AI feature detection model.

7. The method of claim 1, wherein analyzing the dermoscopic image comprises providing the detected or selected features to a decision-tree model.

8. The method of claim 1, wherein the detected features comprise dermoscopic features, attributes of dermoscopic features, and/or clusters of dermoscopic features, wherein:
a dermoscopic feature comprises one or more of a dot, clod, pseudopod, structureless, circle, or blood vessel,
an attribute of a dermoscopic feature comprises one or more of a symmetry, color, thickness, or location, and
a cluster of dermoscopic features comprises a pattern formed by a plurality of dermoscopic features.

9. The method of claim 1, wherein the dermoscopic image is a polarized dermoscopy, PD, image.

10. The method of claim 1, wherein displaying the detected features comprises overlaying the detected features on the dermoscopic image, preferably wherein one or more of the features is highlighted, colored in, outlined, cut out, and/or marked with a symbol.

11. A device (400) for indicating a likelihood of a skin condition in an image, comprising
a display (430),
a user input mechanism (430), and
a processor (410) configured to perform operations corresponding to the method of any of claims 1 to 10.

12. The device of claim 11, further comprising a communication unit (440) configured to obtain the dermoscopic image from an external device (480).

13. A computer program comprising instructions which, when executed by a computer, cause the computer to carry out the method of claim 1.

14. A system comprising the device (400) and the external device (480) of claim 12.

* * * * *